(12) United States Patent
Price

(10) Patent No.: US 10,888,087 B2
(45) Date of Patent: Jan. 12, 2021

(54) LACTAM SOLUBILITY

(71) Applicant: Conopco, Inc., Englewood Cliffs, NJ (US)

(72) Inventor: Paul Damien Price, Wirral (GB)

(73) Assignee: Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 15/750,906

(22) PCT Filed: Jul. 28, 2016

(86) PCT No.: PCT/EP2016/068010
§ 371 (c)(1),
(2) Date: Feb. 7, 2018

(87) PCT Pub. No.: WO2017/029093
PCT Pub. Date: Feb. 23, 2017

(65) Prior Publication Data
US 2018/0220643 A1  Aug. 9, 2018

(30) Foreign Application Priority Data

Aug. 20, 2015  (EP) .................................... 15181858

(51) Int. Cl.
| A01N 25/02 | (2006.01) |
| A01N 43/36 | (2006.01) |
| A61Q 17/00 | (2006.01) |
| A61K 8/49 | (2006.01) |
| C07D 207/38 | (2006.01) |
| C07D 207/44 | (2006.01) |

(52) U.S. Cl.
CPC ............. A01N 25/02 (2013.01); A01N 43/36 (2013.01); A61K 8/4913 (2013.01); A61Q 17/005 (2013.01); C07D 207/38 (2013.01); C07D 207/44 (2013.01)

(58) Field of Classification Search
CPC ........ A01N 25/00; A01N 43/36; A61K 8/345; A61K 8/4913; C07D 207/38
See application file for complete search history.

(56) References Cited

U.S. PATENT DOCUMENTS

| 5,955,419 | A | 9/1999 | Barket, Jr. et al. | |
| 7,985,722 | B2 | 7/2011 | DeSanto | |
| 8,641,948 | B2 | 2/2014 | Ghogh et al. | |
| 9,586,901 | B2 * | 3/2017 | Kumar ................. | C07D 207/36 |
| 9,930,888 | B2 * | 4/2018 | Parry ..................... | A61K 8/922 |
| 10,306,886 | B2 * | 6/2019 | Price ........................ | A61K 8/34 |
| 10,561,142 | B2 * | 2/2020 | Parry ................... | A61K 8/4913 |
| 2007/0269473 | A1 | 11/2007 | Nelson | |
| 2009/0175810 | A1 | 7/2009 | Winckle | |
| 2011/0059144 | A1 | 3/2011 | Fletcher et al. | |
| 2012/0190667 | A1 | 7/2012 | Ghogh et al. | |
| 2013/0142855 | A1 | 6/2013 | Gross et al. | |
| 2013/0190377 | A1 | 7/2013 | Kumar et al. | |
| 2014/0017287 | A1 | 1/2014 | Lei et al. | |
| 2014/0294925 | A1 | 10/2014 | Yin | |
| 2014/0296336 | A1 | 10/2014 | Berndl et al. | |
| 2015/0073069 | A1 | 3/2015 | De Gans et al. | |
| 2015/0351393 | A1 | 12/2015 | Parry et al. | |

FOREIGN PATENT DOCUMENTS

| CN | 1169112 | 12/1997 | | |
| CN | 1688543 | 10/2005 | | |
| CN | 101410372 | 4/2009 | | |
| CN | 102257117 | 11/2011 | | |
| CN | 103260609 | 8/2013 | | |
| WO | WO2004016588 | 2/2004 | | |
| WO | WO2006085089 | 8/2006 | | |
| WO | WO2007008504 | 1/2007 | | |
| WO | WO2007085042 | 8/2007 | | |
| WO | WO-2007085042 A1 * | 8/2007 | ........... | C07D 207/36 |
| WO | WO-2010069742 A1 * | 6/2010 | ........... | C11D 3/2096 |
| WO | WO-2012156250 A1 * | 11/2012 | ............... | C11D 1/86 |
| WO | WO2014118240 | 8/2014 | | |
| WO | WO-2014118240 A1 * | 8/2014 | ............. | A01N 25/30 |
| WO | WO2017029112 | 2/2017 | | |

OTHER PUBLICATIONS

Neodol 25-7 Product Page. Shell Chemicals published 2018 (Year: 2018).*
Kerwin (Polysorbate 20 and 80 used in the formulation of protein biotherapeutics: structure and degradation pathway, Journal of Pharmaceutical Science vol. 97, pp. 2924-2937 published 2008) (Year: 2008).*
Carla S.M. Pereira et al., Ethyl lactate as a solvent: properties, applications and production processes—a review, Green Chemistry, 2011, pp. 2658-2671; XP055235519, vol. 13, No. 10.
IPRP in PCTEP2016069072, Aug. 2, 2017.
IPRP2 in PCTEP2016068585, Nov. 2, 2017.
IPRP2 in PCTEP2016068625, Sep. 6, 2017.
Mary E. Davey et al., Rhamnolipid Surfactant production Affects Biofilm Architecture in Pseudomonas aeruginosa PAO1, Journal of Bacteriology, 2003, pp. 1027-1036, vol. 185, No. 3, American Society for Microbiology.
Ondrej Krenk et al., Methodology for Synthesis of Enantiopure 3,5-Disubstituted Pyrrol-2-ones, European Journal of Organic Chemistry, 2015, pp. 5414-5423; XP002752111.
Search Report & Written Opinion in EP15181849, dated Feb. 23, 2016.
Search Report & Written Opinion in PCTEP2016069072, dated Sep. 14, 2016.
Search Report and Written Opinion in PCTEP2016067613, dated Sep. 21, 2016.
Report and Written Opinion in PCTEP2016067616, dated Sep. 12, 2016.

(Continued)

*Primary Examiner* — Timothy P Thomas
*Assistant Examiner* — George W Kosturko
(74) *Attorney, Agent, or Firm* — Foley & Lardner LLP

(57) ABSTRACT

Compositions comprising lactams and non-ionic surfactants, suitable for use as antimicrobial, anti-biofilm and bacteriostatic compositions.

10 Claims, No Drawings

(56) References Cited

OTHER PUBLICATIONS

Report and Written Opinion in PCTEP2016068008, dated Sep. 12, 2016.
Report and Written Opinion in PCTEP2016068010, dated Sep. 12, 2016.
Report and Written Opinion in PCTEP2016068287, dated Oct. 26, 2016.
Report and Written Opinion in PCTEP2016068585, dated Oct. 4, 2016.
Report and Written Opinion in PCTEP2016068625, dated Sep. 9, 2016.
Report in EP15181842, dated Dec. 10, 2015.
Report in EP15181846, dated Dec. 10, 2015.
Report in EP15181847, dated Dec. 17, 2015.
Report in EP15181851, dated Dec. 11, 2015.
Report in EP15181856, dated Dec. 14, 2015.
Search Report in EP15181858, dated Dec. 11, 2015.
Von R. Scheffold Und P. Dubs, Synthese von Azaprotoanemoninen, Helvetica Chimica Acta, 1967, pp. 798-808; XP55249911.
Written Opinin in EP15181856, dated Dec. 14, 2015.
Written Opinion 2 in PCTEP2016067613, dated Jul. 11, 2017.
Written Opinion in EP15181842, dated Dec. 10, 2015.
Written Opinion in EP15181846, dated Dec. 11, 2015.
Written Opinion in EP15181847, dated Dec. 17, 2015.
Written Opinion in EP15181851, dated Dec. 11, 2015.
Written Opinion in EP15181858, dated Dec. 11, 2015.
Wei et al.; Measurement and Correlation of the Solubility of Penicillin V Potassium in Ethanol + Water and 1-Butyl Alcohol + Water Systems; Journal of Chemical and Engineering Data; 2015; 112-117; vol. 60, No. 1.
Borate et al.; Novel hybrids of fluconazole and furanones: Design, synthesis and antifungal activity; Bioorganic & Medicinal Chemistry Letters; 2011; pp. 4873-4878; vol. 21.
Munoz, et al.; Enzymatic enantiomeric resolution of phenylethylamines; Org. Biomol. Chem.; 2011; pp. 8171-8177 (abstract only—total 5 pages); vol. 9.
Paulusse, et al.; Journal of Polymer Science: Part A: Polymer Chemistry, vol. 44, 5445-5453 (2006).
https://news.illinois.edu/view/6367/207368. Ultrasonication can induce polymer scission, polymerization, and block co-polymer formation; downloaded Jun. 8, 2020.
Mohd, et al. Ultrasonic Modification of Micelle Structures, Handbook of Ultrasonics and Sonochemistry. Springer, Singapore Received Oct. 9, 2015, Abstract; downloaded Jun. 8, 2020.

\* cited by examiner

LACTAM SOLUBILITY

This application claims priority from EP 15181858.0 filed 20 Aug. 2015 which is herein incorporated by reference for all purposes.

The present invention relates to compositions comprising lactams and non-ionic surfactants. The compositions are suitable for use as, for example, antimicrobial anti-biofilm and bacteriostatic compositions.

WO 2007/085042 and WO 2004/016588 disclose lactams for antimicrobial benefit and steps towards their synthesis. WO2014/118240 discloses antimicrobial compositions comprising a lactam and a hydrotope.

However, use of these lactams is limited by compatibility with certain formulations and, in particular, solubility in certain aqueous solutions.

The present invention relates to compositions comprising lactams and non-ionic surfactants. The inventor(s) have found that, surprisingly, the presence of a non-ionic surfactant advantageously improves lactam solubility.

More specifically, the present invention relates to compositions comprising lactams as described in WO 2007/085042 and WO 2004/016588, the contents of which, and in particular the lactam structures explicitly drawn out therein, are incorporated by reference. The compositions further comprise a non-ionic surfactant.

For example, in a first aspect, the present invention relates to a compositions comprising a lactam and a non-ionic surfactant, wherein the lactam is a lactam of formula (I) or (II):

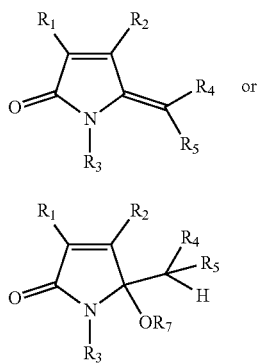

wherein:

$R_1$ and $R_2$ are each independently selected from hydrogen, halogen, alkyl, cycloalkyl, alkoxy, oxoalkyl, alkenyl, heterocyclyl, heteroaryl, aryl and aralalkyl; and $R_3$ is selected from hydrogen, hydroxyl, alkyl, cycloalkyl, alkoxy, oxoalkyl, alkenyl, heterocyclyl, heteroaryl, cycloalkyl, aryl, aralalkyl and —C(O)CR$_6$=CH2;

$R_4$ and $R_5$ are independently selected from hydrogen, aryl, heterocyclyl, heteroaryl, and arylalkyl; and $R_6$ is selected from hydrogen and methyl; and $R_7$ is selected from hydrogen and —C(O)CR$_6$=CH$_2$; and Preferably, at least one of $R_4$ and $R_5$ is hydrogen.

It will be appreciated that, where appropriate groups may be optionally substituted. Optional substituents may include halogens, $C_{1-4}$alkyl, $C_{1-4}$haloalkyl (for example, $CF_3$) and $C_{1-4}$alkoxy.

Alkyls may, for example, be $C_{1-12}$alkyls, such as $C_{1-6}$alkyls. Aryls may, for example, be $C_{6-10}$aryls, for example, phenyls.

Preferably, at least one of $R_1$ and $R_2$ is selected from heterocyclyl, heteroaryl, aryl and arylalkyl.

Preferably, $R_1$ is hydrogen. Preferably, $R_3$ is hydrogen. Preferably, $R_4$ is hydrogen.

Preferably, $R_5$ is hydrogen. Preferably, $R_6$ is hydrogen. Preferably, $R_7$ is hydrogen.

Preferably, $R_2$ is aryl or aralalkyl. More preferably, $R_2$ is a phenyl group or a substituted phenyl group, for example, a mono-substituted phenyl group. Substitution may be ortho, meta, or para. Preferably, it is para. Preferred substituents include halogen and methyl.

For example, and without limitation, $R_2$ may be selected from phenyl, 4-fluorophenyl, 4-chlorophenyl, 4-bromophenyl and 4-methylphenyl.

Accordingly, in a first aspect, the present invention may provide a composition comprising a lactam and a non-ionic surfactant, wherein the lactam is a lactam of Formula Ia or Formula IIa:

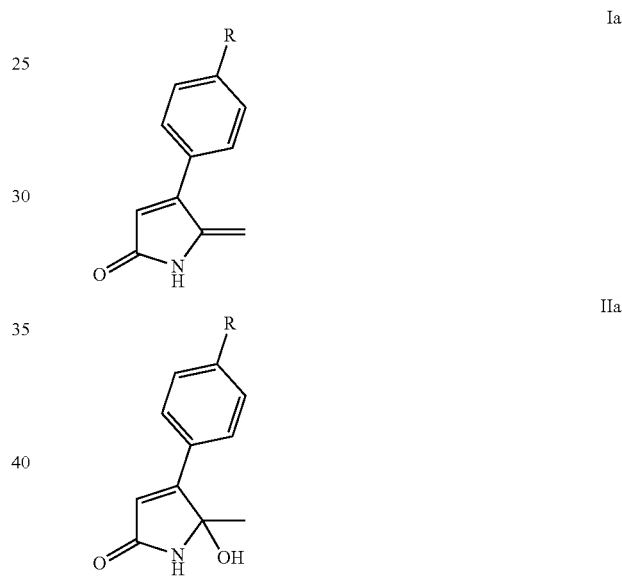

wherein R is H, halogen (preferably, F, Cl, or Br), or $C_{1-4}$alkyl (preferably methyl).

In some embodiments, the lactam is a lactam of formula Ia. In some embodiments, the lactam is a lactam of formula IIa.

Preferred lactams may include:

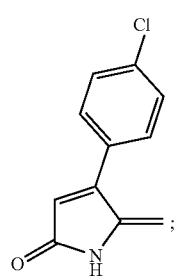

4-(4-chlorophenyl)-5-methylene-pyrrol-2-one (Ref. 488);

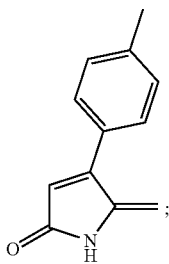

5-methylene-4-(p-tolyl)pyrrol-2-one (Ref. 491)

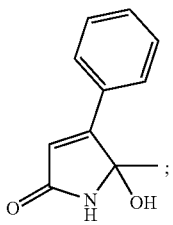

4-phenyl-5-hydroxy-5-methyl-1H-pyrrol-2-one (Ref. 131)

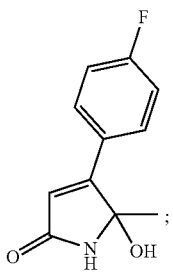

4-(4-fluorophenyl)-5-hydroxy-5-methyl-1H-pyrrol-2-one (Ref. 258)

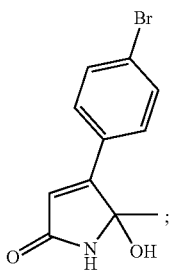

4-(4-bromophenyl)-5-hydroxy-5-methyl-1H-pyrrol-2-one (Ref. 316).

The composition may be, without limitation, any of a personal care composition, a homecare composition, a pharmaceutical composition, or an industrial composition such as an anti-biofilm coating or paint, for example, for use in maritime environments. The composition may also be an agricultural chemical. The compositions may be suitable for use as antimicrobial, anti-biofilm and bacteriostatic compositions. Non-limiting examples of such compositions are provided herein. The compositions may also be used as additive compositions; in other words, the composition may be combined with further ingredients such as excipients to form a composition as described above.

Suitably, the composition is an aqueous composition. It may be a non-aqueous composition.

Preferably the composition contains 0.000001 to 50% wt. lactam, more preferably 0.001 to 50% wt. even more preferably 0.01 to 5% wt, most preferably 0.01 to 2%.

In some cases, the non-ionic surfactant may be a polysorbate (in other words, a PEG-ylalated sorbitan esterified with a fatty acid. Polysorbates are commercially available and often called polysorbate XX or Tween® XX, wherein XX denotes the total number of PEG units.

Suitable polysorbates may include polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate). Preferred non-ionic surfactants may include Tween® 20.

In some cases, the no-ionic surfactant may be a fatty acid alkoxylates, for example an ethoxylate. The fatty acid alkoxylate may have a $C_{8-35}$ alkyl or alkenyl chain, preferably a $C_{10-18}$ alkyl or alkenyl chain, most preferably a $C_{10-18}$ alkyl chain such as a $C_{10-12}$ alkyl chain or a $C_{12-15}$ alkyl chain. It will be appreciated that alkyl and alkenyl chains may be branched or straight chain. The fatty acid ethoxylate may have, for example, from 3 to 25, more preferably 5 to 15 ethylene oxide groups, for example, Neodol® surfactants. A preferred surfactant is a $C_{12-15}$ alcohol ethoxylate having 7 ethylene oxide groups. This may be referred to as Neodol® 25-7.

In other words, the non-ionic surfactant may be a fatty acid ethoxylate of formula (II):

$$Alk-(OCH_2)_pOH \qquad (II)$$

wherein p is 3 to 25, preferably 5 to 15, more preferably 5 to 10, most preferably 7; and Alk is a $C_{8-35}$ alkyl or alkenyl chain, preferably a $C_{10-15}$ alkyl chain, for example a $C_{10-15}$ alkyl chain, for example a $C_{12-15}$ alkyl chain.

The composition may comprise up to 20% wt. non-ionic surfactant, for example up to 15% wt. Suitably, the amount of non-ionic surfactant is up to 10% wt. of the composition. For example, the composition may comprise 0.01 to 10% wt. surfactant, such as 0.1 to 10% wt, optionally 1 to 10% wt. In some cases, the amount of non-ionic surfactant may be up to 9% wt., 8% wt., 7% wt., 6% wt., 5% wt, 4% wt., 3% wt. or even up to 2% wt. As demonstrated herein, very small amount of surfactant may be used and still provide enhanced solubility. For example, the amount may be less than 2% wt, for example less than 1.5% wt., less than 1% wt. and in some cases as low as 0.5% wt.

The ratio of lactam to non-ionic surfactant may, for example, be from 1:0.5 to 1:20, preferably from 1:0.5 to 1:10, such as from 1:0.5 to 1:5.

DESCRIPTION

Lactams may be obtained using methods as described in WO 2007/085042 and WO 2004/016588, which are herein incorporated by reference in their entirety.

Non-Ionic Surfactant

For the purposes of this disclosure, 'non-ionic surfactant' shall be defined as amphiphilic molecules with a molecular weight of less than about 10,000, unless otherwise noted, which are substantially free of any functional groups that exhibit a net charge at the normal wash pH of 6-11.

Any type of non-ionic surfactant may be used, although preferred materials are further discussed below. Highly preferred are fatty acid alkoxylates, especially ethoxylates, having a $C_{8-35}$ alkyl or alkenyl chain, preferably a $C_{8-30}$ alkyl or alkenyl chain, more preferably a $C_{10-24}$ alkyl or alkenyl chain chain, especially a $C_{10-18}$ alkyl or alkenyl chain, alkyl groups may be preferred, and having preferably 3 to 25, more preferred 5 to 15 ethylene oxide groups, for example, Neodol® surfactants, available from Shell® (The Hague, The Netherlands); ethylene oxide/propylene oxide block polymers which may have molecular weight from 1,000 to 30,000, for example, Pluronic® from BASF (Ludwigshafen, Germany); and alkylphenol ethoxylates, for example Triton X-100®, available from Dow Chemical® (Midland, Mich., USA).

Other non-ionic surfactants may be preferred. These include condensates of alkanolamines with fatty acids, such as cocamide DEA, polyol-fatty acid esters, such as the Span series available from Uniqema® (Gouda, The Netherlands), ethoxylated polyol-fatty acid esters, such as the Tween® series available from Uniqema (Gouda, The Netherlands), alkylpolyglucosides, such as the APG line available from Cognis® (Dusseldorf, Germany) and n-alkylpyrrolidones, such as the Surfadone® series of products marketed by ISP (Wayne, N.J., USA).

For example, the non-ionic surfactant may be a non-ionic surfactant of comprising an esterified sorbitan, such as a non-ionic surfactant of formula (III):

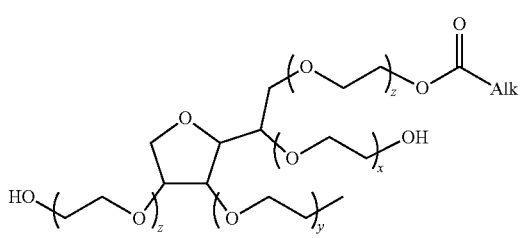

(III)

wherein w+x+y+z is 0 to 20, and n is alkyl or alkenyl. For example w+x+y+z may be 0, as in the Span series available from Uniqema®; and Alk may be $C_{8-35}$, for example, $C_{10-24}$, especially $C_{10-18}$. For example, in Span monopalmitate, Alk is $C_{15}$ alkyl, while in Span 20, Alk is $C_{11}$ alkyl.

For example, w+x+y+z may be 20, as in the Tween® series, also referred to as polysorbates. Suitable polysorbates may include polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate), polysorbate 80 (polyoxyethylene (20) sorbitan monooleate).

The non-ionic surfactant may be an alkyl polysaccharide, for example of formula IV:

wherein R is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is from 0 to about 10, preferably 0; and x is from 1.3 to about 10, preferably from 1.3 to about 2.7. The glycosyl is preferably derived from glucose. To prepare these compounds, the alcohol or alkylpolyethoxy alcohol is formed first and then reacted with glucose, or a source of glucose, to form the glucoside (attachment at the 1-position). The additional glycosyl units can then be attached between their 1-position and the preceding glycosyl unit's 2-, 3-, 4- and/or 6-position, preferably predominantly the 2-position.

Furthermore, non-ionic surfactants not specifically mentioned above, but within the definition, may also be used.

Of course, it will be appreciated that more than one non-ionic surfactant may be used; in other words, the compositions may comprise more than one non-ionic surfactant as described herein. In this case, the amounts of non-ionic surfactant disclosed herein refer to the total amount of non-ionic surfactant.

Compositions

The compositions described herein may be compositions having anti-microbial activity. In some cases, the compositions are anti-bacterial. They may have bactericidal and/or bacteriostatic activity. The inventor(s) have observed desirable bacteriostatic activity. Accordingly, in some cases, the composition is a bacteriostatic composition.

The compositions may also prevent and/or inhibit biofilm formation. Biofilms are formed when microorganisms stick to a surface. Biofilm extracellular polymeric substances may be formed. Biofilms (also referred to as slime) present problems in industrial environments; for example, they may form in pipes in apparatus, or industrial and agricultural structures, on solar panels, and on boat hulls and other marine structures. Biofilms may also pose a problem in domestic environments. For example, biofilms may form in domestic appliances such as washing machines. Biofilms are also present in personal care, for example, they may form on tooth surfaces.

Compositions suitable for any and all of these applications are within the scope of the invention. In some cases, the composition is a paint or other coating. In such cases, the composition may further comprise a binder, optionally a pigment and optionally one or more conventional additives (for example, to modify surface tension, improve flow properties, improve the finished appearance, increase wet edge, improve pigment stability, etc—such additives are known in the art). The composition may comprise an aqueous solvent or an organic solvent to suit purpose.

The composition may also be used in medical applications, for example to coat equipment including medical devices.

In some cases, the composition is a pharmaceutical composition. In other words, the composition may comprise a lactam as described herein and a pharmaceutically acceptable excipient. The composition may be suitable for topical use (for example, it may be a cream or lotion), it may be suitable for ocular use (for example, it may be an used as a pharmaceutical eye drop), it may be suitable for otic use (for example, it may be used as an ear drop), it may be suitable as a mouth wash, or it may be suitable for oral administration.

In some cases, the composition is a composition suitable for use in the home (often referred to as a homecare composition) or institutions. Homecare compositions include, without limitation, cleaning products, laundry detergents, and fabric conditioners. In some cases, the composition is a homecare composition, for example a laundry liquid. The composition may therefore comprise a detergent surfactant and a builder. The composition may be a fabric conditioner (also called a fabric softener) and may comprise an antistatic agent. The composition may also be a domestic cleaning product.

In some cases, the composition is a personal care composition. For example, the composition may be intended for use on the skin (for example, a cream, cleanser or serum). For example, the composition may be useful in the prevention or treatment of acne. For example, the composition may comprise one or more of dimethicone, petrolatum, a humectant such as hyaluronic acid or glycerin; and ceramide(s). In some cases, the composition is a personal care composition comprising a detergent, for example, the composition may be a face wash or shower gel or hair shampoo. The composition may be a hair treatment composition other than a shampoo. The composition may be a deodorant composition (for example, a deodorant powder, paste or liquid). The composition may be an oral care composition (such as a toothpaste or mouthwash and may include, for example, fluoride and/or flavourings.

In some cases, the composition is a contact lens cleaning fluid.

The composition may be a composition suitable for use in agriculture, for example, as a soil additive (solid or liquid).

The composition may be a composition suitable for use in the treatment of or manufacture of glass or lens for example as an additive/treatment for solar panels.

EXAMPLES

Screening of NIS

The following representative example uses 4-(4-chlorophenyl)-5-methylene-pyrrol-2-one.

Excess solid lactam (~3 mg) was placed in a Whatman® Mini Uniprep sample vial, fitted with a 0.45 um nylon filter. Water or water+additive (NIS) (500 μL) was added the mixture shaken and tapped briefly to initially disperse the solid and the mixture then agitated for 48 hours using a plate shaker fitted with a vial holder. After 48 hours, the solid was removed from the system by pressing down the plunger with integral filter on the vial. This removes the solid and provides filtered solution within the inner chamber which is then ready for analysis.

The level of lactam dissolved in solution was quantified using HPLC analysis. Samples were analysed on an Agilent 1200® series HPLC fitted with a Thermo Hypersil Gold® C18 column (15×2.1×3 μm), isocratic elution with 60/40 methanol/water (+0.1% Formic Acid), 0.4 mL/min flow rate, using a DAD detector at 285 nm. The lactam tested has a retention time of ~2.8 minutes.

For each additive, the absolute level of lactam in solution was measured and reported as an increase in solubility of lactam relative to water alone.

Each test surfactant solution was tested in triplicate and the mean value of lactam in solution calculated. Values of solubility were quoted as the improvement in aqueous solubility vs water alone (i.e. mean level of lactam dissolved in water+solvent/mean level of lactam dissolved in water) to allow comparison between screens conducted on different days.

| Additive | % Additive in Water | Mean Lactam Level in Solution (ppm) | Solubility Increase vs water alone |
|---|---|---|---|
| Neodol 25-7 | 0 | 2.4 | 1.0 |
| | 0.5 | 116.0 | 48.3 |
| | 1 | 203.2 | 84.7 |
| | 2 | 390.4 | 162.7 |
| | 5 | 603.3 | 251.4 |
| | 10 | 612.5 | 255.2 |
| | 20 | 455.6 | 189.8 |

-continued

| Additive | % Additive in Water | Mean Lactam Level in Solution (ppm) | Solubility Increase vs water alone |
|---|---|---|---|
| Tween 20 | 0 | 1.7 | 1.0 |
| | 0.5 | 61.6 | 36.9 |
| | 1 | 118.3 | 70.9 |
| | 2 | 226.5 | 135.8 |
| | 5 | 518.3 | 310.7 |
| | 10 | 829.6 | 497.3 |
| | 20 | 1546.3 | 927.0 |
| Tween 80 | 0 | 6.0 | 1.00 |
| | 0.5 | 41.5 | 6.92 |
| | 1 | 75.0 | 12.51 |
| | 2 | 123.3 | 20.56 |
| | 5 | 208.4 | 34.74 |
| | 10 | 391.4 | 65.23 |
| | 0.5 | 50.5 | 18.9 |
| | 1 | 104.9 | 39.1 |
| | 2 | 170.7 | 63.7 |
| | 5 | 432.4 | 161.3 |
| | 10 | 942.3 | 351.6 |
| | 20 | 1490.8 | 556.3 |
| | 0.1 | 15.2 | 5.7 |
| | 0.5 | 42.6 | 15.9 |
| | 1 | 77.5 | 28.9 |
| | 2 | 139.6 | 52.1 |

The inventor(s) have demonstrated that non-ionic surfactants are beneficial at increasing lactam solubility in water, in particular at lower concentrations. The best examples are Tween® 20 and Neodol® 25-7.

---oOo---

It will be appreciated that, except where expressly provided otherwise, all preferences are combinable.

The invention claimed is:

1. A composition comprising a lactam and 0.5% wt. to 20% wt of a non-ionic surfactant, wherein
   the lactam is

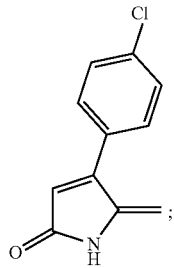

and
   the non-ionic surfactant is a $C_{12}$-$C_{15}$ alcohol ethyoxylate with 6.5-7.6 moles of ethylene oxide to alcohol.

2. The composition of claim 1, wherein the composition comprises less than 2% wt. non-ionic surfactant.

3. The composition of claim 1, wherein the composition comprises between 5% to 15% wt. of the $C_{12}$-$C_{15}$ alcohol ethyoxylate with 6.5-7.6 moles of ethylene oxide to alcohol.

4. The composition of claim 1, wherein the composition comprises 5% to 11% wt. of the $C_{12}$-$C_{15}$ alcohol ethyoxylate with 6.5-7.6 moles of ethylene oxide to alcohol.

5. The composition of claim 1, wherein the composition comprises 9% to 11% wt. of the $C_{12}$-$C_{15}$ alcohol ethyoxylate with 6.5-7.6 moles of ethylene oxide to alcohol.

6. The composition of claim 1, wherein the composition comprises 4% to 7% wt. of the $C_{12}$-$C_{15}$ alcohol ethyoxylate with 6.5-7.6 moles of ethylene oxide to alcohol.

7. The composition of claim 1, wherein the ratio of lactam to non-ionic surfactant is from 1:0.5 to 1:1.

8. The composition of claim 1, wherein the ratio of lactam to non-ionic surfactant is from 1:1 to 1:10.

9. The composition of claim 1, wherein the ratio of lactam to non-ionic surfactant is from 1:10 to 1:100.

10. The composition of claim 1, wherein the ratio of lactam to non-ionic surfactant is from 1:1 to 1:1000.

\* \* \* \* \*